United States Patent
Liphardt et al.

(10) Patent No.: US 7,554,662 B1
(45) Date of Patent: Jun. 30, 2009

(54) SPATIAL FILTER MEANS COMPRISING AN APERTURE WITH A NON-UNITY ASPECT RATIO IN A SYSTEM FOR INVESTIGATING SAMPLES WITH ELECTROMAGNETIC RADIATION

(75) Inventors: Martin M. Liphardt, Lincoln, NE (US); Ping He, Lincoln, NE (US); Blaine D. Johs, Lincoln, NE (US); Craig M. Herzinger, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 370 days.

(21) Appl. No.: 11/648,060

(22) Filed: Dec. 29, 2006

Related U.S. Application Data

(63) Continuation-in-part of application No. 11/204,929, filed on Aug. 15, 2005, now Pat. No. 7,468,794, and a continuation-in-part of application No. 10/699,540, filed on Nov. 1, 2003, now Pat. No. 7,158,231, and a continuation-in-part of application No. 10/178,723, filed on Jun. 24, 2002, now Pat. No. 6,950,182.

(51) Int. Cl.
*G01J 4/00* (2006.01)
(52) U.S. Cl. .................... 356/369; 356/445
(58) Field of Classification Search .......... 356/364–369
See application file for complete search history.

(56) References Cited

U.S. PATENT DOCUMENTS

| | | | | |
|---|---|---|---|---|
| 3,905,675 A | 9/1975 | McCracken | ................. | 350/17 |
| 4,053,232 A | 10/1977 | Dill et al. | ................. | 356/369 |
| 4,877,960 A | 10/1989 | Messerschmidt et al. | .... | 250/341 |
| 4,996,120 A | 2/1991 | Smothers et al. | ............... | 430/2 |
| 5,032,734 A | 7/1991 | Orazio, Jr. et al. | .......... | 250/572 |
| 5,148,323 A | 9/1992 | Campbell et al. | ........... | 359/738 |
| 5,329,357 A | 7/1994 | Bernoux et al. | ............. | 356/369 |
| 5,373,359 A | 12/1994 | Woollam et al. | ............. | 356/328 |
| 5,414,559 A | 5/1995 | Burghardt et al. | ........... | 359/623 |
| 5,426,506 A | 6/1995 | Ellingson et al. | ............ | 356/369 |
| 5,504,582 A | 4/1996 | Johs et al. | ................... | 356/369 |
| 5,517,312 A | 5/1996 | Finarov | ...................... | 356/386 |
| 5,521,706 A | 5/1996 | Green et al. | ................. | 356/369 |
| 5,608,526 A | 3/1997 | Piwonka-Corle et al. | .... | 356/369 |
| 5,666,201 A | 9/1997 | Johs et al. | ................... | 356/369 |
| 5,684,642 A | 11/1997 | Zumoto et al. | .............. | 359/740 |
| 5,796,521 A | 8/1998 | Kahlert et al. | ............. | 359/619 |
| 5,859,424 A | 1/1999 | Norton et al. | ............... | 250/226 |
| 5,872,630 A | 2/1999 | Johs et al. | ................... | 356/369 |
| 5,877,859 A | 3/1999 | Aspnes | ....................... | 356/364 |
| 5,889,593 A | 3/1999 | Bareket | ...................... | 356/445 |
| 5,910,842 A | 6/1999 | Piwonka-Corle et al. | .... | 356/369 |
| 5,917,594 A | 6/1999 | Norton | ........................ | 356/327 |
| 5,963,327 A | 10/1999 | He et al. | ..................... | 356/369 |

(Continued)

OTHER PUBLICATIONS

"Automatic Rotating Element Ellipsometers: Calibration, Operation and Real-Time Applications", Collins, Rev. Sci. Instrum., 61(8) (1990).

*Primary Examiner*—L. G Lauchman
(74) *Attorney, Agent, or Firm*—James D. Welch

(57) ABSTRACT

Systems which utilize electromagnetic radiation to investigate samples and include at least one spatial filter which has an aperture having a hole therethrough with a non-unity aspect ratio.

20 Claims, 8 Drawing Sheets

U.S. PATENT DOCUMENTS

| | | | |
|---|---|---|---|
| 6,134,012 A | 10/2000 | Aspnes et al. | 356/369 |
| 6,184,984 B1 | 2/2001 | Lee et al. | 356/369 |
| 6,321,601 B1 | 11/2001 | Maris | 73/657 |
| 7,145,654 B2 | 12/2006 | Norton | 356/369 |
| 7,158,231 B1 * | 1/2007 | Woollam et al. | 356/369 |
| 7,468,794 B1 * | 12/2008 | Liphardt et al. | 356/369 |

* cited by examiner

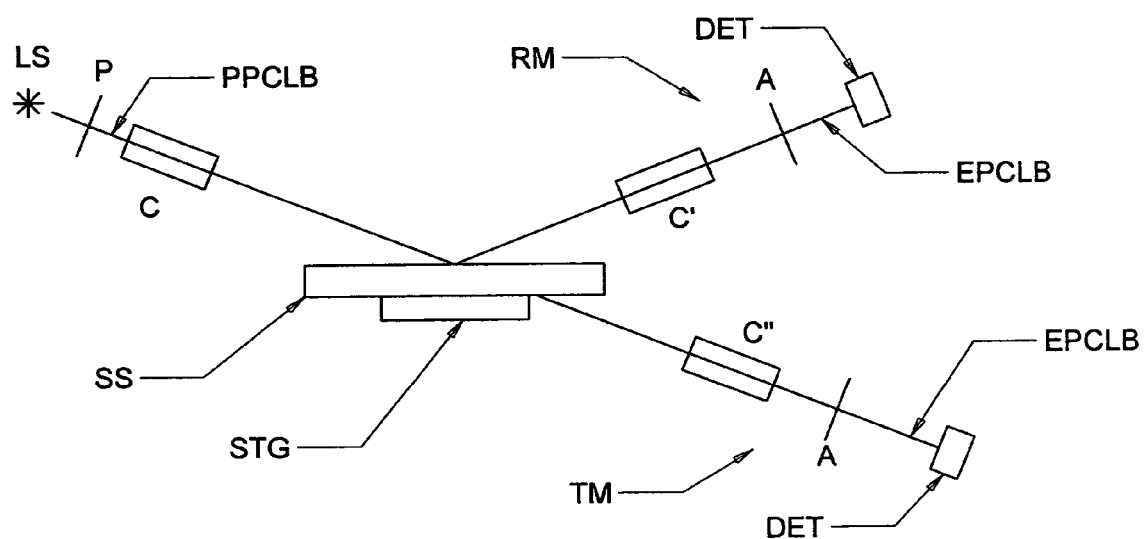
FIG. 1a₁
PRIOR ART
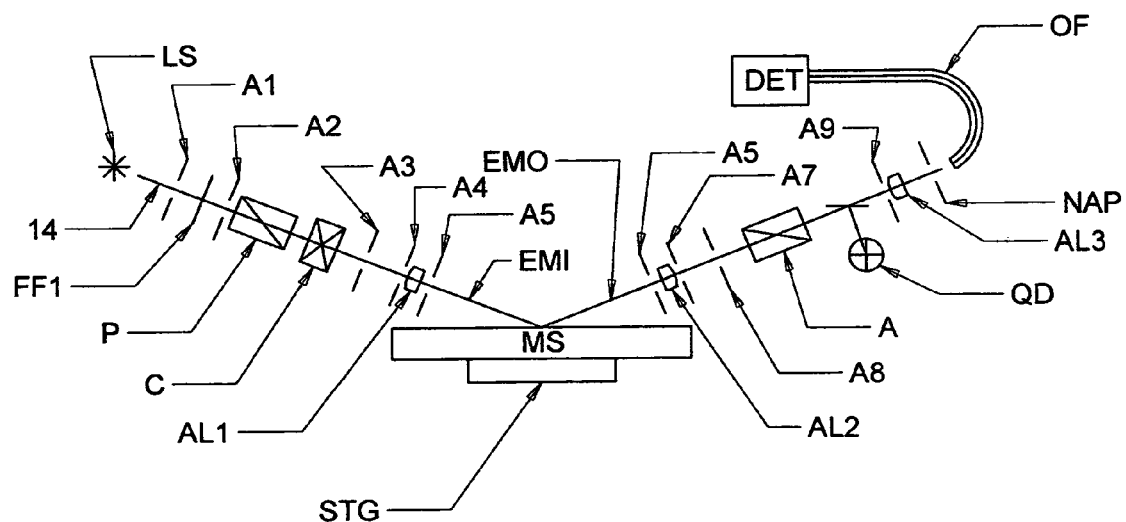
FIG. 1a₇

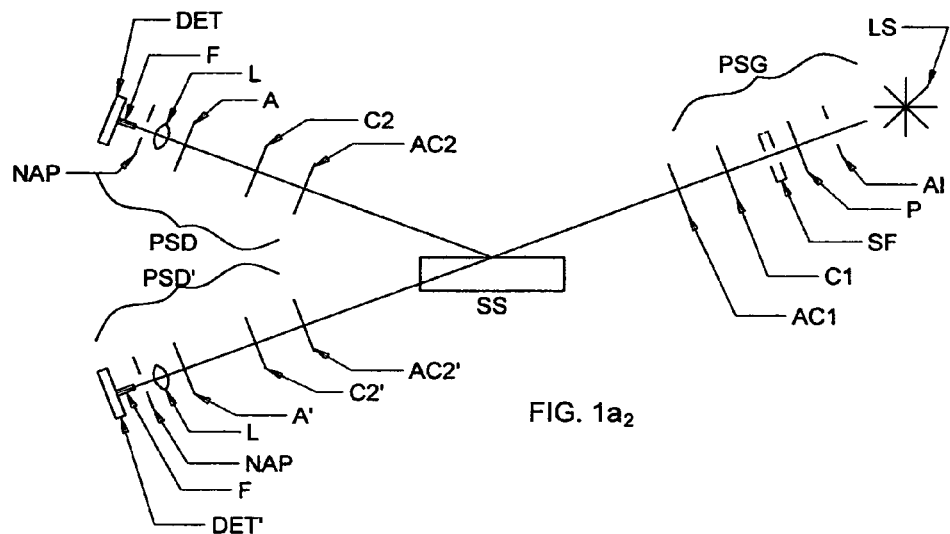
FIG. 1a₂
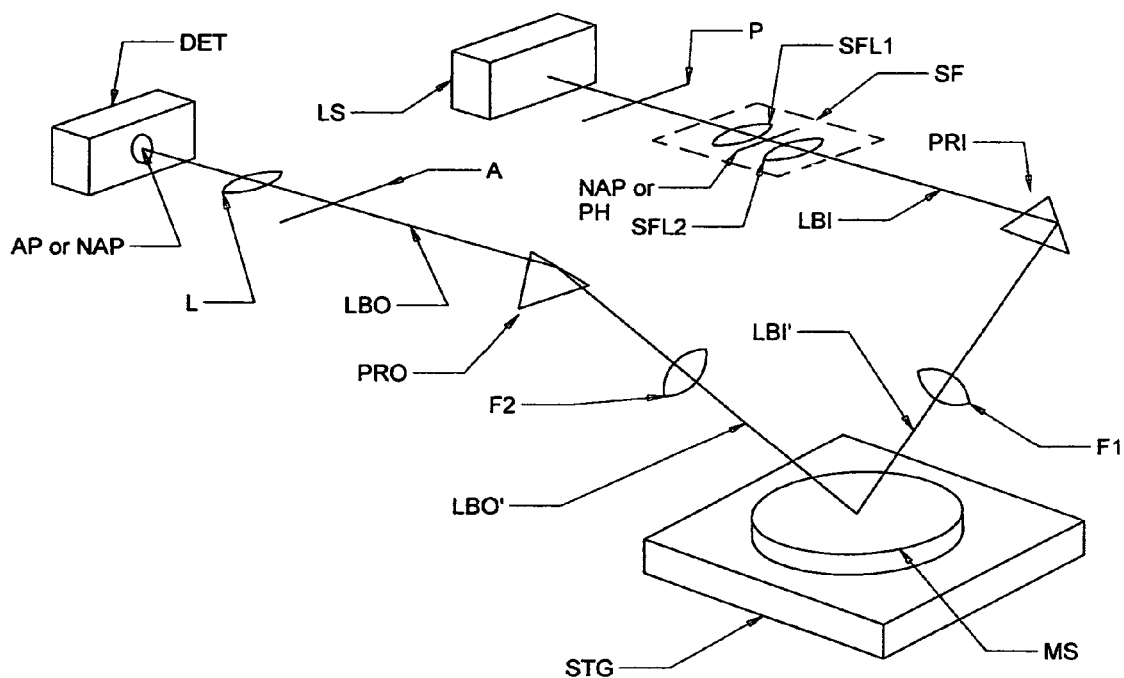
FIG. 1a₃

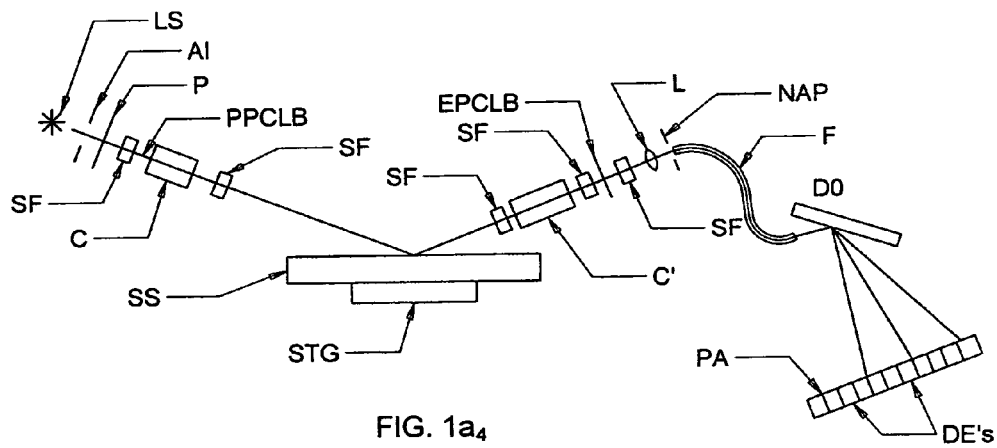
FIG. 1a₄
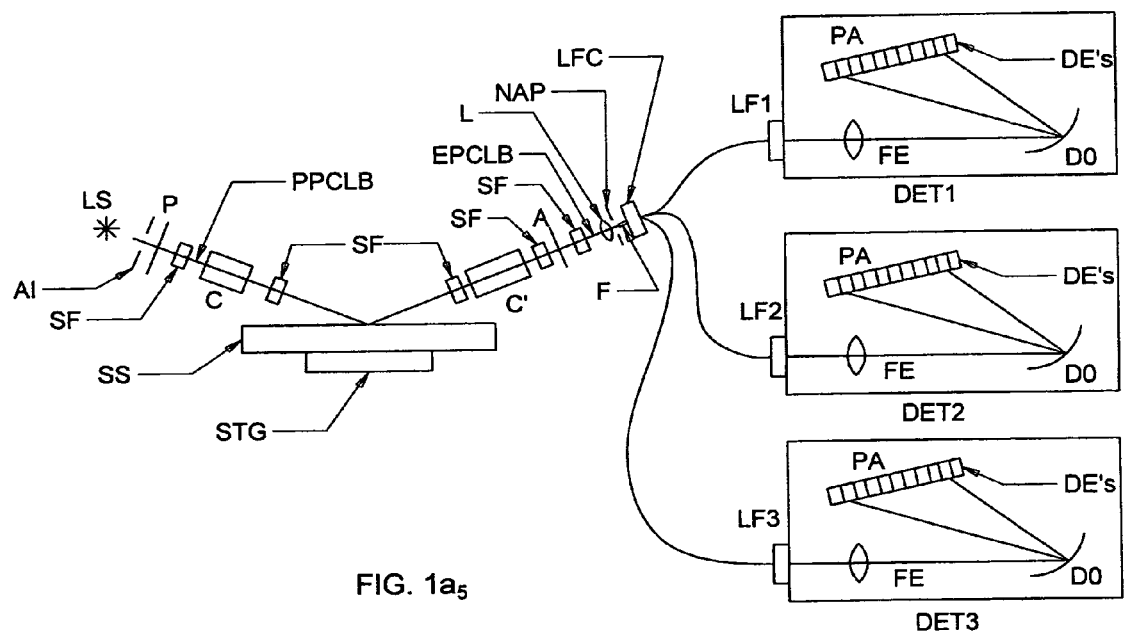
FIG. 1a₅

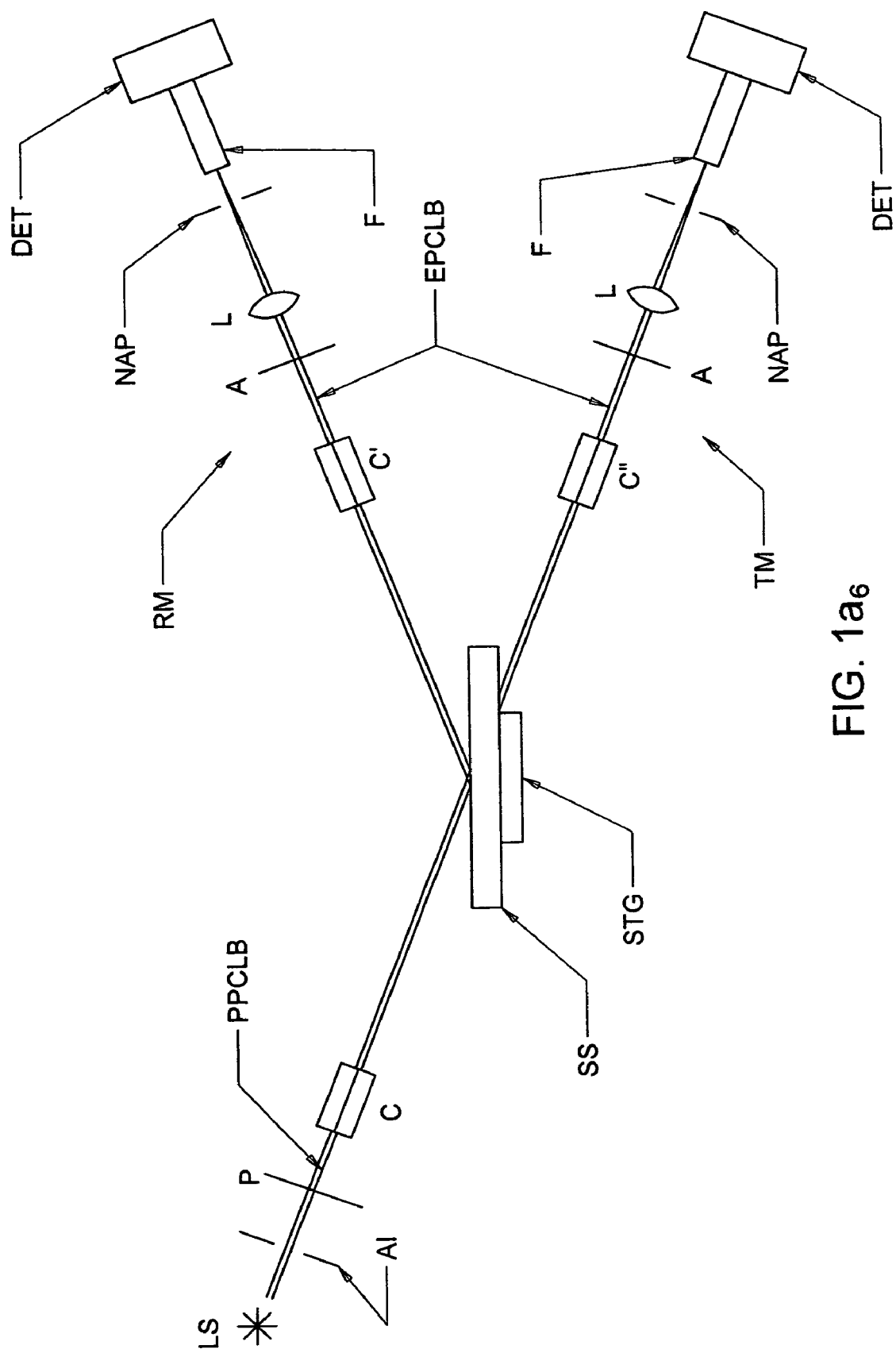
FIG. 1a₆

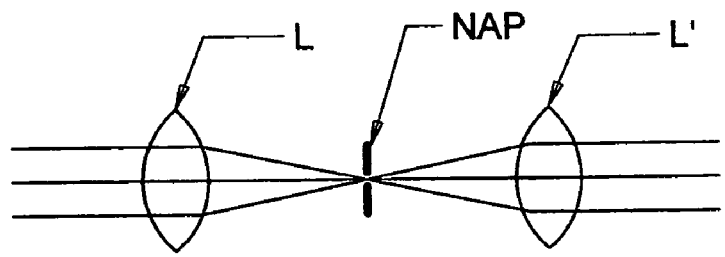
FIG. 5a
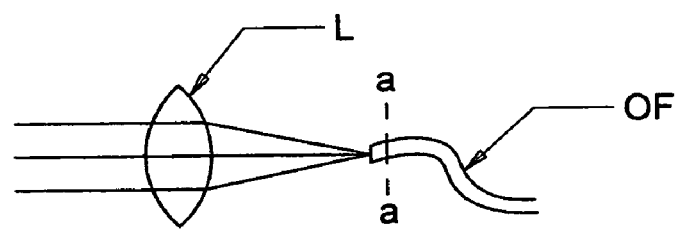
FIG. 5b1
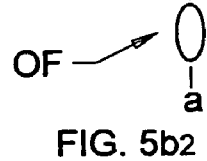
FIG. 5b2
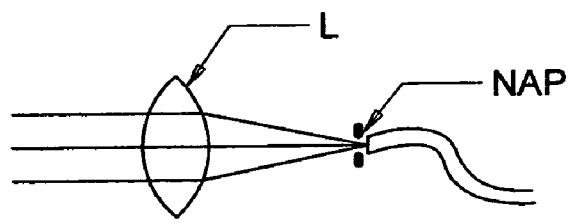
FIG. 5c
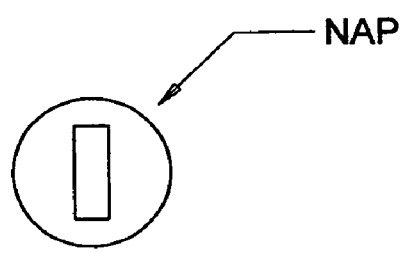
FIG. 5d1
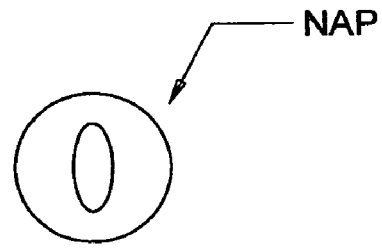
FIG. 5d2

SPATIAL FILTER MEANS COMPRISING AN APERTURE WITH A NON-UNITY ASPECT RATIO IN A SYSTEM FOR INVESTIGATING SAMPLES WITH ELECTROMAGNETIC RADIATION

This Application is a CIP of application Ser. No. 11/204,929 Filed Aug. 15, 2005 now U.S. Pat. No. 7,468,794 and therevia is a CIP of application Ser. No. 10/178,723 Filed Jun. 24, 2002, (now U.S. Pat. No. 6,950,182); and is also a CIP from application Ser. No. 10/699,540 Filed Nov. 1, 2003 (now U.S. Pat. No. 7,158,231).

TECHNICAL FIELD

The present invention relates to systems which utilize electromagnetic radiation to investigate samples, and more particularly to systems which utilize electromagnetic radiation to investigate samples which comprise at least one spatial filter which comprises an aperture having a hole therethrough with a non-unity aspect ratio.

BACKGROUND

Not limited to, but particularly in the case where an electromagnetic beam is utilized to investigate a sample system which presents with a varying depth surface topology, it is important to provide an electromagnetic beam of a known lateral dimension and which presents with a relatively simple cross-sectional intensity profile.

It is noted that often electromagnetic beams present with a substantially arbitrary intensity profile, with the highest intensity being located centrally, which intensity generally decreasing as with increasing radius. While an arbitrary beam intensity profile is typically acceptable for use in ellipsometry and related practices, it has been found that once the intensity of a substantially arbitrary profile beam of electromagnetic radiation has decreased to, as an arbitrary example, say 10% of its peak, it does not always continue to decay directly to essentially zero (0.0). Instead, it often presents irregularly as a function of radius, (eg. easily visualized as being generally similar to the Fourier transform of a square wave), and such irregular intensity content can adversely affect ellipsometer performance. The cause of said irregular intensity profile can include such as optical element wavelength dependent diffraction, surface roughness or other non-idealities, and where electromagnetic radiation is provided via an aperture or via the end of a light fiber contained in a cladding, electromagnetic radiation falling outside a geometric image thereof is often of an irregular intensity content.

It would be of benefit, as regards obtaining accurate data from application of ellipsometers and the like systems, if the intensity of an electromagnetic beam could be forced to decay quickly to zero (0.0), rather than demonstrate an irregular intensity profile as a function of radius in an outer annulus region.

With an eye to the present invention, a Search of Patents was conducted. Perhaps the most relevant Patent identified is a recent Patent to Norton, U.S. Pat. No. 7,145,654, where the system therein is described as utilizing a beam focused onto the end of an optical fiber, such that the angular range of the probe beam is less than a natural numerical aperture of an optical fiber. The purpose of the Norton invention is to selectively attenuate and reduce the presence of secondary maxima falling outside a measurement spot on a sample. Minimizing said secondary maxima can improve the amount of light measured by a detector that is reflected from inside a measurement spot. Said 654 patent is included herein by reference.

A U.S. Pat. No. 5,517,312 to Finarov describes application of a scattered light reducing system at the entry to a Detector in a Rotating Analyzer or Rotating Polarizer Ellipsometer System, which scattered light reducing system consists of two lenses with a hole containing diaphragm located midway therebetween, and at the focal lengths of said lenses. Said scattered light reducing system is present after a sample system and processes electromagnetic radiation after it interacts with said sample system. The pin-hole is described as serving to reduce scattered light and providing high spatial resolution.

Another Patent identified is that to Campbell et al., U.S. Pat. No. 5,148,323. Said 323 patent describes a Spatial Filter in which a pinhole is located other than at the focal length of a converging lens.

U.S. Pat. No. 3,905,675 to McCraken describes a Spatial Filter containing system which enables observation of a weak source of electromagnetic radiation in the presence of strong sources thereof.

U.S. Pat. No. 5,684,642 to Zumoto et al., describes an optical transmission system for use in fashioning an electromagnetic beam for use in machining materials which combines a Spatial Filter and an Optical Fiber.

U.S. Pat. No. 4,877,960 to Messerschmidt et al. is identified as it describes masking energy from outside the target area in a microscope having dual remote image masking.

A U.S. Pat. No. 5,329,357 to Bernoux et al. is identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this Patent is not controlling where electromagnetic radiation carrying fiber optics are present.

Continuing, Spectroscopic Ellipsometer Systems are also known in the art. Application a Spatial Filters near a Detector, in the context of Rotating Polarizer and Rotating Analyzer Ellipsometer Systems has been reported, (see U.S. Pat. No. 5,517,312 to Finerov). It is noted, that application of Spatial Filters in Rotating Compensator Ellipsometer Systems, such as the Rotating Compensator Ellipsometer System Claimed in co-owned U.S. Pat. No. 5,872,630, has been described in Co-Pending application Ser. No. 11/204,929 by the inventors herein. Said 630 patent and 929 application, are incorporated by reference hereinto and are co-owned with this Application.

For general reference, a Patent to Dill et al., U.S. Pat. No. 4,053,232 is disclosed as it describes a Rotating-Compensator Ellipsometer System which operates utilizing monochromatic light. Further, a Patent to Aspnes et al., U.S. Pat. No. 5,877,859 is disclosed as it describes a Broadband Spectroscopic Rotating Compensator Ellipsometer System wherein the Utility is derived from selecting a wavelength range and compensator so that at least one wavelength in said wavelength range has a retardation imposed of between 135 and 225 degrees, and another wavelength in said wavelength range has a retardation imposed which is outside that retardation range. Further Patents of general interest of which the Inventors are aware include those to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to ellipsometer systems. A Patent to He et al., U.S. Pat. No. 5,963,327 is also disclosed as it describes a laterally compact ellipsometer system which enables providing a focused polarized beam of electromagnetic radiation at an oblique angle-of-incidence to a sample system in a small spot area.

In addition to the identified Patents, certain Scientific papers are also identified.

A Review paper by Collins, titled "Automatic Rotating Element Ellipsometers Calibration, Operation and Real-Time Applications", Rev. Sci. Instrum., 61(8) (1990), is identified for general information.

Even in view of the known art, in the context of rotating compensator ellipsometer systems, a need remains for a system and methodology of its use, which adds spatial filter means before and/or after a sample system, to, for instance, fashion a beam with a radially essentially arbitrary Profile which directly approaches zero intensity.

DISCLOSURE OF THE INVENTION

The present invention is a system for investigating samples with electromagnetic radiation having an equivalent to a spatial filter integrated therewithin. A preferred embodiment comprises:
  a) a source of electromagnetic radiation;
  b) a first aperture;
  c) a stage for supporting a sample;
  d) a focusing means;
  e) a second aperture, said second aperture having a hole therethrough with an aspect ratio other than unity;
  f) an optical fiber; and
  d) a detector.

In use said source of electromagnetic radiation provides a beam of electromagnetic radiation, at least some of which passes through said first aperture and proceeds to interact with a sample placed on said stage for supporting a sample, said beam, after interaction with said sample being caused to be focused by said focusing means and pass through said second aperture, then enter said optical fiber, which directs it into said detector.

Said integrated equivalent to a spatial filter comprising said first aperture, said focusing means, said second aperture and said optical fiber, said elements being relatively positioned with respect to one another such that said focusing means images electromagnetic radiation passing through said first aperture, at the location of said second aperture, and such that at least some of said imaged electromagnetic radiation passing through said second aperture enters said optical fiber.

Said system can further comprise a polarizer between said source of electromagnetic radiation and said stage for supporting a sample, and an analyzer between said stage for supporting a sample and said detector and the result is an ellipsometer or polarimeter. Further, said system can also comprise at least one rotatable or rotating compensator located at, at least one location selected from the group consisting of:
  between said source of electromagnetic radiation and said stage for supporting a sample; and
  between said stage for supporting a sample and said detector.

The just described system can further comprise a second spatial filter present between said source of electromagnetic radiation and said detector, said second spatial filter comprising a sequence of:
  a focusing means;
  an aperture having a hole therethrough with an aspect ratio selected from the group consisting of:
    unity; and
    other than unity; and
  a collimating means.

In use said source of electromagnetic radiation provides a beam of electromagnetic radiation, at least some of which is directed to interact with a sample placed on said stage for supporting a sample, said beam, after interaction with said sample being caused to enter said detector, at least some of said electromagnetic radiation that reaches said detector also pass passing through said spatial filter.

A modified embodiment of a system for investigating samples with electromagnetic radiation including a spatial filter, comprises:
  a) a source of electromagnetic radiation;
  b) a stage for supporting a sample;
  c) a detector;

said system further comprising a spatial filter present between said source of electromagnetic radiation and said detector, said spatial filter comprising a sequence of:
  a focusing means;
  an aperture having a hole therethrough with an aspect ratio other than unity; and
  a collimating means;
  such that electromagnetic radiation passing therethrough is focused by said focusing means to the location of the hole in said aperture, and such that electromagnetic radiation passing through said spatial filter is re-collimated by said collimating means;

said source of electromagnetic radiation, in use, providing a beam of electromagnetic radiation, at least some of which is directed to interact with a sample placed on said stage for supporting a sample, said beam, after interaction with said sample being caused to enter said detector, at least some of said electromagnetic radiation that reaches said detector also passes through said spatial filter.

A preferred embodiment of the present invention system for investigating samples with electromagnetic radiation, having an equivalent to a spatial filter integrated therewithin, comprises:
  a) a source of electromagnetic radiation;
  b) a first aperture;
  c) a first focusing means;
  d) a stage for supporting a sample;
  e) a second focusing means;
  f) a second aperture, said second aperture having a hole therethrough with an aspect ratio other than unity;
  g) an optical fiber; and
  h) a detector.

In use said source of electromagnetic radiation provides a beam of electromagnetic radiation, at least some of which passes through said first aperture and is focused onto a sample placed on said stage for supporting a sample, said beam, after interaction with said sample being caused to be focused by said focusing means and pass through said second aperture, then enter said optical fiber, which directs it into said detector. Said integrated equivalent to a spatial filter comprising said first aperture, said focusing means, said second aperture and said optical fiber, said elements being relatively positioned with respect to one another such that said focusing means images electromagnetic radiation passing through said first aperture, at the location of said second aperture, and such that at least some of said imaged electromagnetic radiation passing through said second aperture enters said optical fiber.

As with the first embodiment, the foregoing embodiments can further comprise a polarizer between said source of electromagnetic radiation and said stage for supporting a sample, and an analyzer between said stage for supporting a sample and said detector and the result is an ellipsometer or polarimeter. Further, said system can also comprise at least one rotatable or rotating compensator located at, at least one location selected from the group consisting of:

between said source of electromagnetic radiation and said stage for supporting a sample; and between said stage for supporting a sample and said detector.

It is specifically noted that a common thread in both embodiments is that there is present at least one spatial filter related aperture which has a hole therein with a non-unity aspect ratio, (ie, the hole has different orthogonal component dimension lengths and is not, for instance circular or square, but rather is, for instance, instead, respectively oval, elliptical or rectangular etc.).

It is also to be understood that making the angular range of the beam of electromagnetic radiation, (after its interaction with a sample and focusing thereof by said focusing means), less than a natural numerical aperture of an optical fiber, in combination with the use of apertures with non-unity aspect ratio holes therethrough as described in the foregoing, enables achieving very desirable results.

A method of providing a small spot size beam of electromagnetic radiation for application in investigating a sample comprises the steps of:

a) providing a polarized beam of electromagnetic radiation and causing it to pass through a first aperture and thereafter become focused onto a sample with a first focusing means, such that said beam interacts with said sample to the end that energy is tangibly and concretely shifted between orthogonal components thereof;

b) intercepting said beam of electromagnetic radiation after it interacts with said sample with a second focusing means and therewith directing it to image said first aperture in the plane of a second aperture, which second aperture presents with a non-unity aspect ratio, such that at least some of said beam passes through said second aperture and enters an optical fiber;

c) causing said optical fiber to carry the electromagnetic radiation entered thereinto to a detector such that said detector outputs at least one signal; and d) analyzing said at least one signal from said detector to arrive at sample characterizing data.

Said method can further comprise storing or displaying said at least one signal from said detector or said sample characterizing data.

In any of the foregoing the hole in said aperture just prior to the optical fiber which has an aspect ratio other than unity can be characterized by each dimension thereof being a selection from the group consisting of:

said dimension is smaller than the diameter of said optical fiber;

said dimension is the same diameter of said optical fiber; and said dimension is larger than the diameter of said optical fiber.

Finally, it is noted that the purpose of present invention is to selectively attenuate and reduce the presence of secondary maxima falling outside a measurement spot on a sample. Minimization of said secondary maxima improves the amount of light measured by a detector that is reflected from inside a measurement spot on a sample.

The present invention will be better understood by reference to the Detailed Description Section of this Disclosure, in conjunction with the accompanying Drawings.

SUMMARY OF THE INVENTION

It is therefore a primary purpose and/or objective of the present invention to provide means and method for producing a small spot of electromagnetic radiation on a sample.

It is another purpose and/or objective of the present invention to provide an integrated combination of a focusing means, an aperture with a non-unity aspect ratio hole therethrough, and an optical fiber combination in a system for investigating samples with electromagnetic radiation, such that after electromagnetic radiation is caused to interact with a sample, but before entering a detector, it is focused by said focusing means to the location of the non-unity aspect ratio hole in said aperture, and then passes into the end of an optical fiber.

It is another yet purpose and/or objective of the present invention to provide a spatial filter system comprising an aperture with a non-unity aspect ratio hole therethrough.

It is a another purpose yet of the present invention to provide a system for forming a beam of electromagnetic radiation which presents with an intensity profile that radially drops off quickly to zero (0.0) without demonstrating low level oscillations similar to Fourier Transform of a Square Wave characteristics.

It is another purpose and/or objective of the present invention to teach, in the context of an ellipsometer system application of discrete and/or integrated component spatial filter system(s) having apertures with non-unity aspect ratio holes therethrough, to form a beam of electromagnetic radiation which presents with an intensity profile which radially drops off quickly to zero (0.0).

Other purposes and/or objectives of the present invention will become obvious from a reading of the Specification and Claims.

BRIEF DESCRIPTION OF THE DRAWINGS

FIG. 1a1 shows a basic rotating compensator ellipsometer system as previously Patented in U.S. Pat. No. 5,872,630.

FIG. 1a2 shows a general elemental configuration of an ellipsometer system indicating that a conventional Spatial Filter (SF) can be present, said system including a present invention Focusing Means (L) and optical Fiber (F).

FIG. 1a3 shows another general elemental configuration of an ellipsometer system indicating that a conventional Spatial Filter (SF) can be present, said system including a present invention Focusing Means (L) focused on an Aperture (NAP), which can comprise an Optical Fiber present therewithin.

FIGS. 1a4 and 1a5 show that at least one conventional Spatial Filter (SF) can be present at least one location somewhere in the demonstrate Rotating Compensator Ellipsometer System, and that a Means (L) Optical Fiber (F) is present prior to a dispersive optic (DO).

FIG. 1a6 shows the system of FIG. 1a with the Focusing Means (L) and Optical Fiber (F) of the present invention added.

FIG. 1a7 shows the components of a Reflectance Mode Material System Investigation Systems which has five apertures in the pathway of an electromagnetic beam prior to a material system, and four thereafter.

FIG. 2 shows an example of a source of electromagnetic radiation comprising a light fiber, lens, apertures and polarizer.

FIG. 4 shows the effect of the presence of a spatial filter on the radial intensity of an electromagnetic beam as is developed and utilized in spectroscopic rotating compensator ellipsometers.

FIGS. 5a-5c show various approaches to realizing Spatial Filters which can be fitted with apertures having non-unity aspect ratio holes therein.

FIGS. 5d1 and 5d2 show two non-limiting demonstrative designs for apertures having non-unity aspect ratio holes therein.

FIG. 6 is another presentation for a present invention system.

DETAILED DESCRIPTION

Figure 6:
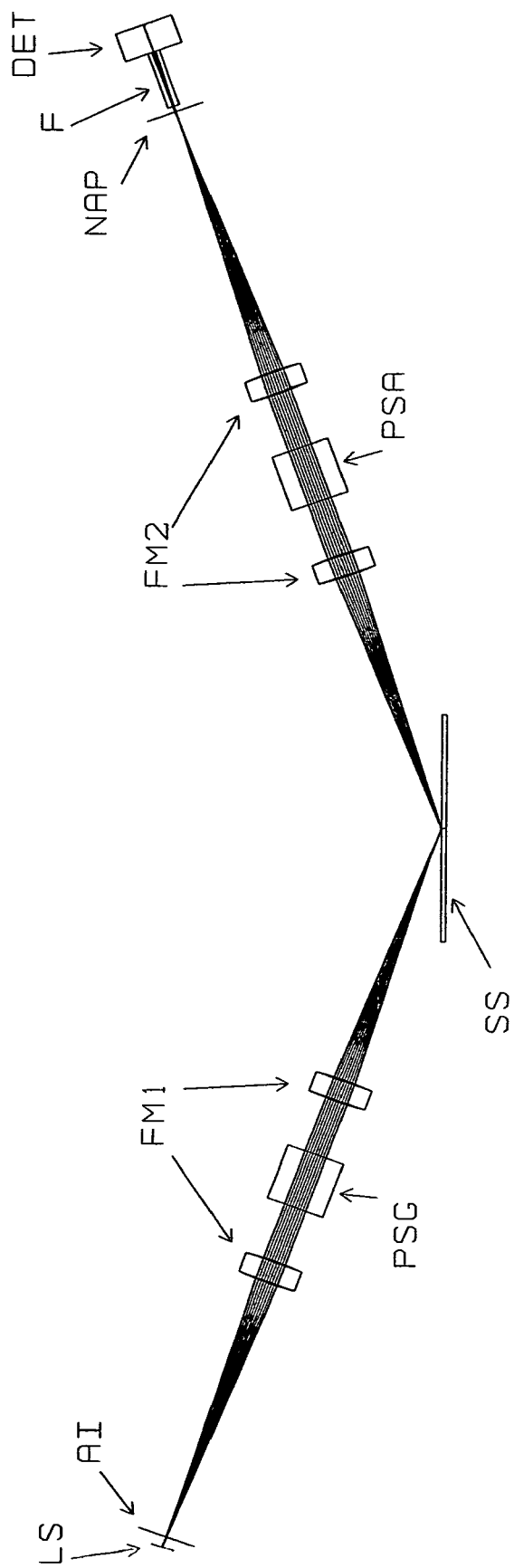

Turning now to the Drawings, there is shown in FIG. 1a1 a demonstrative Ellipsometer system as disclosed in U.S. Pat. No. 5,872,630, demonstrating both reflection and transmission modes, and comprising a Source of Electromagnetic Radiation (LS), a Polarizer (P), Compensator(s) (C) (C') (C"), and a Detector (DET). Source (LS) is shown to provide a beam of electromagnetic radiation (PPCLB), and a beam of electromagnetic radiation (EPCLB) is shown reflecting from/transmitting through a Sample System (SS). FIG. 1a6 shows the integrated spatial filter system added to the system of FIG. 1a1. Note the distinguishing Aperture (AI), Focusing Means (L), Aperture (NAP) and Optical Fiber (F) of the present invention present in FIG. 1a6. In use Aperture (AI), is imaged by Focusing Means (L) to Aperture (NAP). The effect of Aperture (AI), Focusing Means (L), Aperture (NAP), and the Optical Fiber (F) is to eliminate an outer annulus of a beam focused on an end of the Optical Fiber (F), by said Focusing lens as demonstrated by FIG. 4 herein.

Figure 2:
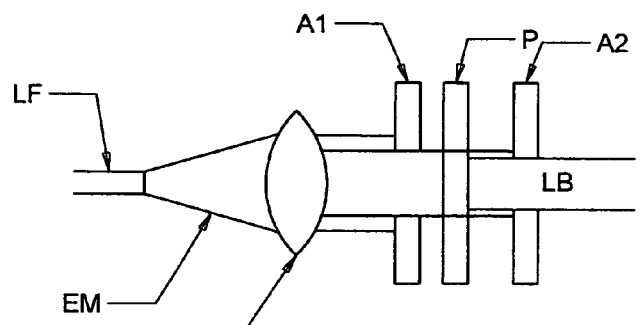

FIG. 1a2 shows a general elemental configuration of an ellipsometer system to which the present invention is applied to investigate a sample system (SS). Shown for reflection and transmission are:
  a. a Source of a beam electromagnetic radiation (LS) and aperture (AI);
  b. a Polarizer (P);
  c. a Compensator (C1);
  d. optional additional element(s) (AC1);
  e. a sample system (SS);
  f. optional additional element(s) (AC2);
  g. a Compensator (C2);
  h. an Analyzer (A);
  i. a Focusing Means (L) and aperture (NAP);
  j. an Optical Fiber (F); and
  i. a Detector System (DET).

The elements identified as (LS), (AI), (P) and (C1) can be considered to form, as a group, a Polarization State Generator (PSG), and the components (C2), (A), (NAP), (F) and (DET) can be considered, as a group, to form a Polarization State Detector (PSD). It is to be understood that the d. and f. optional "additional elements", (AC1) and (AC2), can be considered as being, for instance, optional input and output lenses or perhaps windows in a vacuum chamber. Also note that after the Polarizer (P) there is indicated, in dashed lines, the presence of an optional conventional Spatial Filter (SF). Other optional conventional Spatial Filter (SF) locations in an ellipsometer system, are prior to the Polarizer (P), after the Compensator (C1) or after the Additional Elements (AC1), or on the Detector (DET) side of the Sample System (SS), before or after the additional element(s), (AC2); Compensator (C2); and Analyzer (A), are included in the scope of the present invention. FIG. 1a2 is distinguished by the Aperture (AI), Focusing Means (L), Aperture (NAD) and Optical Fiber (F).

Another embodiment of an ellipsometer system to which the present invention can be applied is shown in FIG. 1a3, which shows a Perspective view of a demonstrative system. FIG. 1a3 shows a Light Source (LS) and a Polarizer (P), which in combination serve to produce a generally horizontally oriented locus Polarized Beam of Electromagnetic Radiation (LBI). Said generally horizontally oriented Polarized Beam of Electromagnetic Radiation (LBI) is caused to interact with Optical Element, (eg. Prism), (PRI), essentially totally internally reflect therein, pass through Focusing Optic (F1) and become a generally vertically oriented locus Polarized Beam of Electromagnetic Radiation (LBI'), then interact with a Sample System (SS) present on a Sample System supporting Stage (STG). FIG. 1a3 shows that said interaction with the Surface (S) of said Sample System (SS) causes a generally vertically oriented Polarized Beam of Electromagnetic Radiation (LBO') to pass through Focusing Optic (F2). FIG. 1a3 show that after passing through Focusing Optic (F2) said generally vertically oriented locus Polarized Beam of Electromagnetic Radiation (LBO') interacts with Optical Element, (eg. Prism), (PRO) and is essentially totally internally reflected thereby to become generally horizontally oriented locus Polarized Beam of Electromagnetic Radiation (LBO), which generally horizontally oriented locus Polarized Beam of Electromagnetic Radiation (LBO) passes through Analyzer (A) and then enters Detector System (DET), via Unity aspect ratio (AP) or Non-unity aspect ratio (NAP) Aperture, for analysis. It is noted that the purpose of the Focusing Optics (F1) is to produce a very Concentrated High Intensity Small Area Polarized Beam of Electromagnetic Radiation (LBI') from Collimated Polarized Beam of Electromagnetic Radiation (LBI). The purpose of Focusing Optic (F2) is to "Re-Collimate" the generally vertically oriented Polarized Beam of Electromagnetic Radiation (LBO') which results from the Focused Polarized Beam of Electromagnetic Radiation (LBI') being Reflected from said Sample System (SS). The Re-Collimated generally vertically oriented Beam of Electromagnetic Radiation (LBI') being identified as generally horizontally oriented Beam of Electromagnetic Radiation (LBO) after it has been caused to interact with Prism (PRO).

Also, as in the FIG. 1a2 case, note that after the Polarizer (P) there is indicated, in dashed lines, the presence of an optional conventional Spatial Filter (SF). Shown are an aperture ((NAP) or (PH)), (through which electromagnetic beam (LB1) passes), a non-unity aspect ratio hole in which is located at essentially a Focal Length distant from each of Lenses (SFL1) and (SFL2), (see FIG. 1a3). Again, while other pre-sample system locations are included in the scope of the invention, the shown location is preferred for systems that include such a conventional Spatial Filter. Note that either of said Lenses (SFL1) and (SFL2) can be replaced with a functionally essentially equivalent mirror. FIG. 1a2 is further distinguished by the Focusing Means (L), Aperture (NAP) and Optical Fiber (F).

Figure 4:
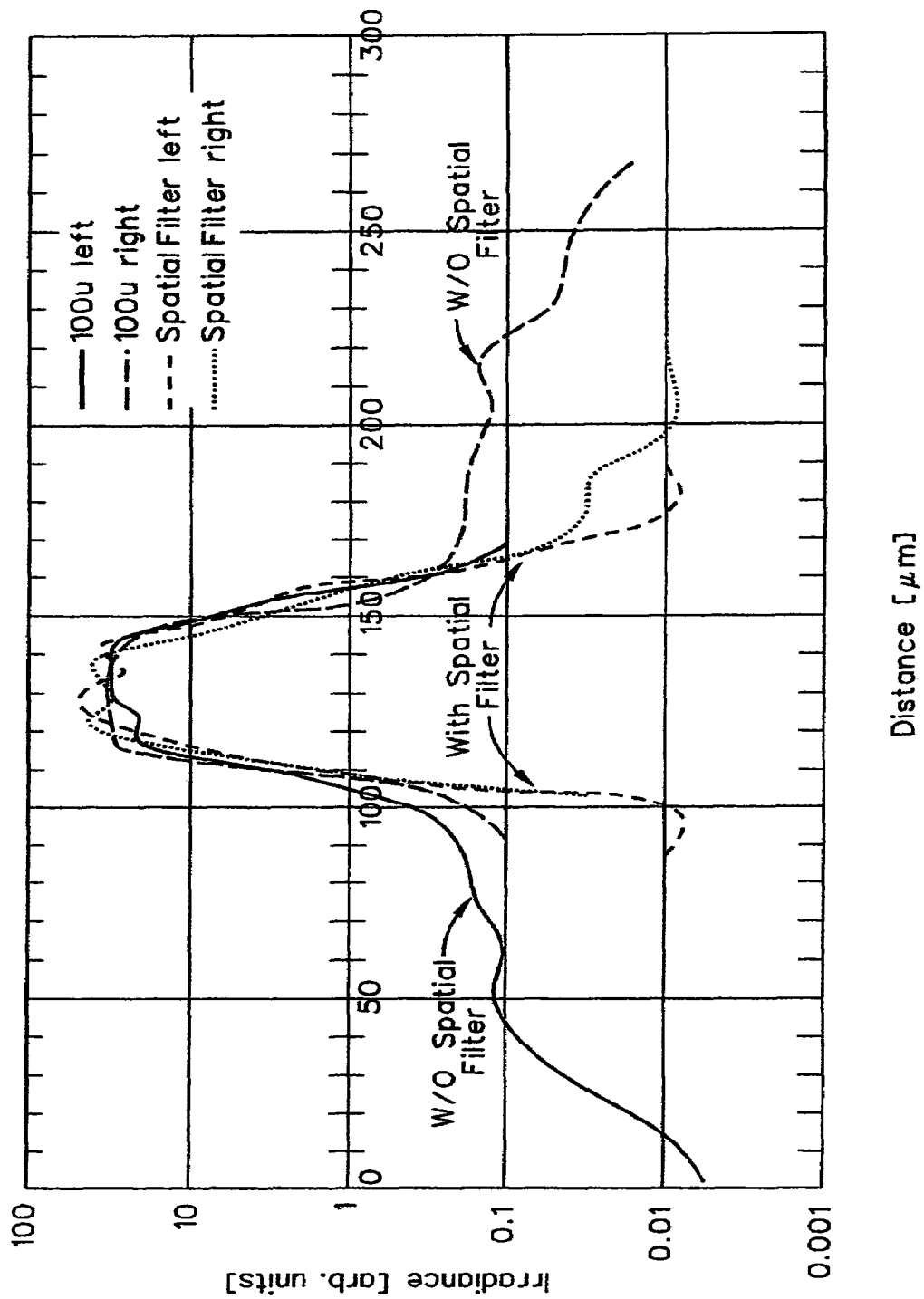

FIG. 1a4 shows a Spectroscopic Reflectance Mode version of the Rotating Compensator Ellipsometer System shown in FIG. 1a1, with the Detector Elements (DE's) containing Photo Array Detector System (DET) shown present directly after the Analyzer (A). FIG. 1a4 is distinguished by the Aperture (AI), Focusing Means (L), Aperture (NAP) and Optical Fiber (F).

FIG. 1a5 shows a Reflectance Mode Rotating Compensator Ellipsometer System configuration in which three (3) Detectors (Det 1), (Det 2) and (Det 3) are fed input by Fiber Optics (LF1), (LF2) and (LF3) present in a Fiber Optic Bundle exiting Fiber Optic Connector (LFC). Note the presence of the integrated Spatial Filter presented by Aperture (AI), Focusing Means (L) and Aperture (NAP). Said Fiber Optic Connector (LFC) receives a Polarized Electromagnetic Beam (EPCLB) exiting the Analyzer (A) via Focusing Means (L) and Aperture (NAP). Said three (3) Detectors (Det 1), (Det 2) and (Det 3) can be, for instance, Off-the-shelf Zeiss Diode Array Spectrometers, and can each comprise a Focusing Element (FE) In functional combination with a Dispersive Optics (DO) and a Diode Element (DE) containing Photo Array (PA). (Zeiss Diode Array Spectrometers provide, for instance, operational wavelength ranges selected from the group consisting of: (300-1150 nm, 190-230 nm, 190-400 nm and 900-2400 nm). It is also mentioned that diffraction grating (DO) can be selected from the group consisting of: (a "lined", a "blazed", and a "holographic" geometry), said lined geometry consisting essentially of symmetrical alternating lines with depressions therebetween, and said blazed geometry consisting of alternating ramp shaped lines with depressions therebetween, and said holographic geometry consisting of continuous cosine shaped lines and depressions), all of which are known in the literature.

Both FIGS. 1a4 and 1a5 show that optional conventional Spatial Filters (SF) can present at, at least one location somewhere in the demonstrative Rotating Compensator Ellipsometer System shown. It is emphasized that said at least one Spatial Filter Equivalent (SF) can be placed anywhere in the Spectroscopic Ellipsometer System. FIG. 1a5 is distinguished by the Focusing Means (L) Non-unity aspect ratio aperture (NAP) and Optical Fiber (F) prior to the Fiber Optic Connector (LFC) which accepts a single input Optical Fibers and provides a plurality thereof as output.

It is also noted that Fiber optics can be utilized to carry Polychromatic Electromagnetic Radiation from a Source thereof (LS) to the position of an Aperture (AI) which can be Non-unity aspect ratio, and Polarizer (P), (see FIGS. 2 and 3a), or from the position of an Analyzer (A) to a Detector (DET) in FIGS. 1a1-1a5, (see for instance (LF1), (LF2), and (LF3) in FIG. 1a5).

Analogically similar figures to those shown in FIGS. 1a3-1a5, but oriented for use in a Transmission Mode are not shown, but should be understood as within the scope of the present invention as implied by FIG. 1a1. Again, the present invention version of such systems are distinguished by the presence of a Aperture (AI), Focusing Means (L), Aperture (NAP) and Optical Fiber (F).

FIG. 1a7 shows the components of a Reflectance Mode Material System Investigation Systems which has five apertures in the pathway of an electromagnetic beam prior to a material system, and four thereafter. For insight, FIG. 1a7 is included to show a preferred polychromatic rotating compensator material system investigation system comprising a source (LS) of polychromatic beam (14) of electromagnetic radiation, a first aperture (A1), a second aperture (A2), a fixed polarizer (P), a rotating compensator (C), a third aperture (A3), a forth aperture (A4), a first substantially achromatic lens (AL1), a fifth aperture (A5), a stage (STG) for supporting a material system (MS), a sixth aperture (A6), a second substantially achromatic lens (AL2), a seventh aperture (A7) an eighth aperture (A8), a fixed analyzer (A), a ninth aperture (A9), a third substantially achromatic lens (AL3), a non-unity aspect ratio aperture (NAP), an optical fiber (OF) and a detector means (DET) which contains a dispersive element and a multiplicity of detector means elements, there typically being a UV filter (FF1) present between said source (LS) of polychromatic beam of electromagnetic radiation and said stage (STG) for supporting a material system. When said polychromatic rotating compensator material system investigation system is used to investigate a material system (MS) present on said stage (STG) for supporting a material system, said fixed analyzer (A) and fixed polarizer (P) are maintained essentially fixed in position and said rotating compensator (C) is caused to continuously rotate while a polychromatic beam of electromagnetic radiation produced by said source (LS) of a polychromatic beam of electromagnetic radiation is sequentially caused to pass through said first aperture (A1), second aperture (A2), fixed polarizer (P), rotating compensator (C), third aperture (A3), forth aperture (A4), first substantially achromatic lens (AL1), fifth aperture (A5), said polychromatic beam of electromagnetic radiation also passing through said UV filter, then interact with a material system (MS) placed on said stage (STG) for supporting a material system (MS), then sequentially pass through said sixth (A6) aperture, second substantially achromatic lens (AL2), seventh aperture (A7), eighth aperture (A8), fixed analyzer (A), ninth aperture (A9), third substantially achromatic converging lens (L), enter said Optical Fiber (OF) and therevia enter said detector means (DET). It is the combination of the Focusing Means (L), Non-unity aspect ratio aperture (NAP) and Optical Fiber (OF) that distinguishes the present invention.

It is also mentioned that in the following it will be generally assumed that a Material System (MS) under investigation by a Spectroscopic Rotating Compensator Ellipsometer System is positioned upon the Material System Supporting Stage (STG). This need not be the case, as is described in U.S. Pat. No. 5,706,087 wherein a Material System (Sample), (MS) can be positioned in a Magneto-Optic System which is physically too large to be supported by said Material System Supporting Stage (STG), or in an environmental control chamber. Further, especially where Ultraviolet range wavelengths are utilized, the system can be placed into an evacuated or purged, (eg. by nitrogen or argon), Chamber to the end that UV absorbing Oxygen and Water Vapor are not present therewithin. The entire system can be so encompassed within a said Chamber, or only the Sample (MS) Stage portion thereof. The Chamber, where utilized, can be of multiple region construction.

Figure 3A:
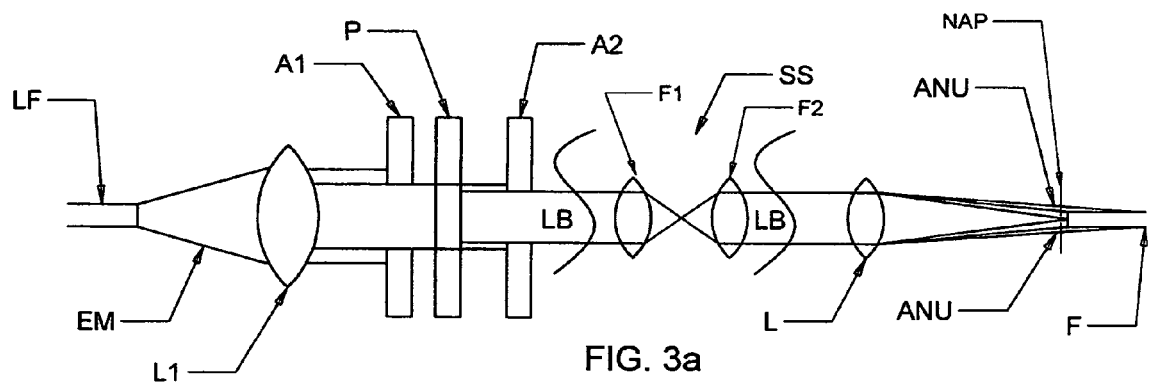
FIG. 3a shows an example of a present invention Focusing Means (L) and Optical Fiber (F) in combination with the system of FIG. 2.

FIG. 2 shows that a Light Source (LS) can comprise a Light Fiber (LF), a Lens (L1), and a First Aperture (A1). In the context of an ellipsometer a Polarizer (P) is also shown as it would be positioned. Shown in addition is a second Aperture (A2). In use electromagnetic radiation (EM) exiting the Light Fiber (LF) expands and enters Lens (L1) and is collimated thereby. First Aperture (A1) limits the beam diameter, and Second Aperture (A2) further does so to provide a beam of electromagnetic radiation labeled (LB). FIG. 3a expands on FIG. 2. FIG. 3a shows beam (LB) entering a Focusing Means (L) and being focused onto and entering the end of Optical Fiber (F). Note however, that an outer Annular (ANU) region of the converged beam does not enter Optical Fiber (F). It is noted that a Focusing Means (F1) can be added to as shown in FIG. 3a to provide a small spot on a sample. The presence of a Sample (SS) is implied, and thereafter is shown a present invention Focusing Means (L), Non-unity aspect ratio aperture (NAP) and Optical Fiber (F) positioned to receive focused electromagnetic radiation (LB) after interaction with said Sample (SS). Note again that the outer annulus of the electromagnetic radiation (LB) after Interaction with said Sample (SS) does not enter said Optical Fiber (F). This effect is emphasized when Non-unity aspect ratio aperture (NAP) is present as shown. However, even without said (NAP) the diameter of the Fiber (F) being smaller than that of the beam can serve to exclude some of the Annular (ANU) region of said Beam (LB).

Figure 3B:
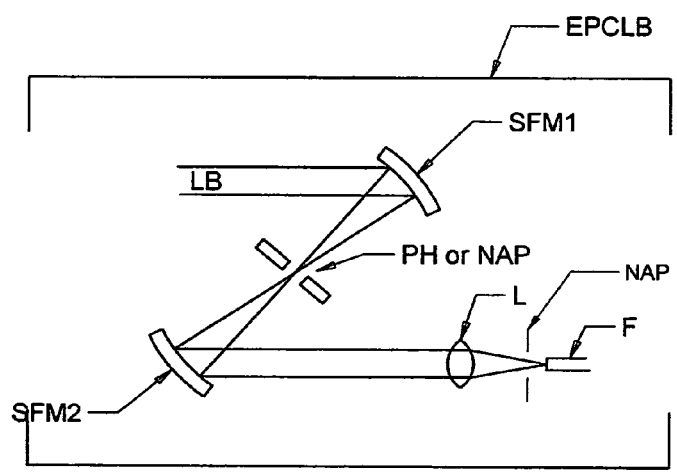
FIG. 3b shows alternative spatial filter construction which can be applied in the context of a FIG. 2 system, including the present invention Focusing Means (L) and Optical Fiber (F).

FIG. 3b shows alternative conventional Spatial Filter (SF) construction in which mirrors (SFM1) and (SFM2) perform the function of lenses (SFL1) and (SFL2) in FIG. 1a3. That is the conventional Spatial Filter shown in FIG. 1a3 can be replaced with that in FIG. 3b. It is further noted that a conventional Spatial Filter could comprise one Lens and one Mirror, in either order in a conventional. Spatial Filter, hence the language "lens or mirror" is to be interpreted broadly as meaning that each is independently selected from the group consisting of a lens and a mirror. Again, the present invention Focusing Means (L) and Optical Fiber (F) are shown, and distinguish the present invention. Note that the Aperture (PH) or (NAP), between Mirrors (SFM1) and (SFM2) can be unity or non-unity aspect ratio, when in combination with a non-unity aspect ratio aperture being present after said Focusing Means (L).

FIG. 4 shows the effect of the presence of the conventional Spatial Filter (SF) as shown in FIG. 1a3 on the Intensity Profile of a beam of electromagnetic radiation passed therethrough. Note that FIG. 4 plots Intensity on a Log Axis, and that the Intensity drops toward 0.001 much quicker when the conventional Spatial Filter is in place than when it is not in place. The present invention combination of a Focusing Means (L), Non-unity aspect ratio aperture (NAP) and Optical Fiber (F) provides a similar result which can be otherwise explained as being the result of the angular range of the beam of electromagnetic radiation, after interaction with said sample and focusing by said Focusing Means (L), being less than a natural numerical aperture of an optical Fiber (OF). It is noted that FIG. 4 demonstrates the effect a present invention Spatial Filter Equivalent has on the size of a spot of electromagnetic radiation which is focused onto a Sample (SS) per se. Note that a smaller spot size is achieved by removing the outer annulus tails which are comprised of maxima and minima.

The present invention also includes, in the context of a spectroscopic ellipsometer and the like systems, the method of removing an radial outer annular ring from an electromagnetic beam by use of an equivalent to a spatial filter. Said method can be recited as a method of processing source electromagnetic radiation beams to eliminate a radially outer annulus thereof, said outer annulus being comprised of low intensity level irregular content, said method comprising placing at least one spatial filter(s) such that said electromagnetic beam passes therethrough. The present invention accomplishes said result by the combined effect of a Focusing Means (L), Non-unity aspect ratio aperture (NAP) and optical Fiber (F) in combination with an imaged Aperture (AI) near the Source (LS) of a beam of electromagnetic radiation as shown in, for instance, FIG. 1a2.

The terminology "outer annular region" as used herein is to be interpreted to mean an outer region of an electromagnetic beam, as distinct from a central region thereof, which outer region appears as an annulus when it is considered that the intensity of the beam decreases to zero as the radius increases to infinity. Said "outer annulus region" at times begins at the point where the intensity of an electromagnetic beam falls to approximately ten (10%) percent of its maximum intensity, and it is noted, might contain approximately two (2%) to five (5%) of the electromagnetic beam's energy content. In a Patent to Norton, U.S. Pat. No. 7,145,654, where a system is described as utilizing a beam focused onto the end of an optical fiber, the effect is described as being the result of the angular range of the probe beam being less than a natural numerical aperture of an optical fiber. Note that no Non-unity aspect ratio aperture (NAP) is recited in Norton 654.

FIGS. 5a-5c show various approaches to realizing Spatial Filters which can be fitted with Apertures (NAP) having non-unity aspect ratio holes therein. FIG. 5a shows a modified conventional spatial filter comprised of a sequence of a Focusing Means (L), an Aperture (NAP) having a Non-unity aspect ratio hole therethrough, followed by a second Focusing Means (L'). FIG. 5b1 shows a functional equivalent to a conventional Spatial Filter comprising Focusing Means (L) and an Optical Fiber (OF). FIG. 5b2 shows that the Optical Fiber (OF) has a Non-unity aspect ratio in cross section taken at a-- --a in FIG. 5b1. FIG. 5c shows a variation on the FIG. 5b1 embodiment wherein the Optical Fiber (OF) is not necessarily of a non-unity aspect ratio, but which has an Aperture (NAP) placed at the focal length of the Focusing Means (L) thereof, just prior to the Optical Fiber (OF). FIGS. 5d1 and 5d2 show two variations of an Aperture (NAP) with a Non-unity aspect ratio hole therethrough.

FIG. 6 is provided to demonstrate that a present invention system can sequentially comprise a Source of electromagnetic radiation (LS), a First Aperture (AI), a Polarization State Generator PSG), a Sample (SS), a Polarization State Analyzer (PSA), a Non-unity ratio aperture (NAP), an Optical Fiber (OF) and a Detector (DET). Importantly, also shown are Focusing Means (FM1) and (FM2), which are each shown as comprising two elements each, one being on either side of the (PSG) and (PSA), respectively. However, it is noted that said two elements (FM1) or (FM2) can both be on one side or the other of the corresponding (PSG) or (PSA).

It is noted that the language "at least partially pass therethrough" regarding an electromagnetic beam interaction with a hole in an Aperture, means that at least a part of said beam passes through the aperture, said part typically being centrally located in said beam, with an annular region being blocked passage.

It is to be understood that a conventional spatial filter basically sequentially consists of beam converging at least one lens and/or mirror, a diaphragm, (ie. aperture), with a pinhole therein located essentially at the focal length of said beam converging lens and/or mirror, and a second beam collimating at least one lens and/or mirror. However, it should be appreciated that, for instance, additional lenses and/or apertures can be added and the resulting system still be within the scope of a conventional spatial filter.

It is also noted that the terminology "outer annulus" refers to the region of an electromagnetic beam which contains maxima and minima which are removed by the present invention.

Further, the terminology "focusing means" can be refractive and/or reflective.

In summary, the present invention is a system which, in use, can be applied to investigate a sample with electromagnetic radiation, said system having a spatial filter or spatial filter equivalent comprising an aperture which contains a hole therein with a non-unity aspect ratio, or an optical fiber with a non-unity aspect ratio. And finally, it should be understood that a non-unity aspect ratio aperture (NAP) can be realized by selecting the geometry of the hole therethrough, and/or by titling/rotating an aperture with a unity or non-unity aspect ratio.

Having hereby disclosed the subject matter of this invention, it should be obvious that many modifications, substitutions and variations of the present invention are possible in light of the teachings. It is therefore to be understood that the present invention can be practiced other than as specifically described, and should be limited in breadth and scope only by the Claims.

We claim:

1. A system for investigating samples with electromagnetic radiation having an equivalent to a spatial filter integrated therewithin, comprising:
   a) a source of electromagnetic radiation;
   b) a first aperture;
   c) a stage for supporting a sample;
   d) a focusing means;
   e) a second aperture, said second aperture having a hole therethrough with an aspect ratio other than unity;
   f) an optical fiber; and
   d) a detector;

such that in use said source of electromagnetic radiation provides a beam of electromagnetic radiation, at least some of which passes through said first aperture and proceeds to interact with a sample placed on said stage for supporting a sample, said beam, after interaction with said sample being caused to be focused by said focusing means and pass through said second aperture, then enter said optical fiber, which directs it into said detector;

said integrated equivalent to a spatial filter comprising said first aperture, said focusing means, said second aperture and said optical fiber, said elements being relatively positioned with respect to one another such that said focusing means images electromagnetic radiation passing through said first aperture, at the location of said second aperture, and such that at least some of said imaged electromagnetic radiation passing through said second aperture enters said optical fiber.

2. A system as in claim 1 which further comprises a polarizer between said source of electromagnetic radiation and said stage for supporting a sample, and an analyzer between said stage for supporting a sample and said detector and in which said system is an ellipsometer or polarimeter.

3. A system as in claim 2, which further comprises at least one rotatable or rotating compensator located at, at least one location selected from the group consisting of:
   between said source of electromagnetic radiation and said stage for supporting a sample; and
   between said stage for supporting a sample and said detector.

4. A system as in claim 1 which further comprises a second spatial filter present between said source of electromagnetic radiation and said detector, said second spatial filter comprising a sequence of:
   a focusing means;
   an aperture having a hole therethrough with an aspect ratio selected from the group consisting of:
      unity; and
      other than unity; and
   a collimating means;

such that in use said source of electromagnetic radiation provides a beam of electromagnetic radiation, at least some of which is directed to interact with a sample placed on said stage for supporting a sample, said beam, after interaction with said sample being caused to enter said detector, at least some of said electromagnetic radiation that reaches said detector also passes through said second spatial filter.

5. A system as in claim 1 which further comprises a focusing means prior to said sample.

6. A system as in claim 1, wherein said hole in said second aperture having an aspect ratio other than unity is characterized by each dimension thereof being a selection from the group consisting of:
   said dimension is smaller than the diameter of said optical fiber;
   said dimension is the same diameter of said optical fiber; and
   said dimension is larger than the diameter of said optical fiber.

7. A system for investigating samples with electromagnetic radiation including a spatial filter, comprising:
   a) a source of electromagnetic radiation;
   b) a stage for supporting a sample;
   c) a detector;

said system further comprising a spatial filter present between said source of electromagnetic radiation and said detector, said spatial filter comprising a sequence of:
   a first focusing means;
   an aperture having a hole therethrough with an aspect ratio other than unity; and
   a collimating means; and
   a second focusing means;
   such that electromagnetic radiation passing therethrough is focused by said first focusing means to the location of the hole in said aperture, and such that electromagnetic radiation passing through said spatial filter is re-collimated by said collimating means; and then is refocused by the second focusing means;

said source of electromagnetic radiation, in use, providing a beam of electromagnetic radiation, at least some of which is directed to interact with a sample placed on said stage for supporting a sample, said beam, after interaction with said sample being caused to enter said detector, at least some of said electromagnetic radiation that reaches said detector also passes through said spatial filter.

8. A system as in claim 7 which further comprises a polarizer between said source of electromagnetic radiation and said stage for supporting a sample, and an analyzer between said stage for supporting a sample and said detector and in which said system is an ellipsometer or polarimeter.

9. A system as in claim 8, which further comprises at least one stationary, rotatable or rotating compensator located at, at least one location selected from the group consisting of:
   between said source of electromagnetic radiation and said stage for supporting a sample; and
   between said stage for supporting a sample and said detector.

10. A method of providing a small spot size beam of electromagnetic radiation for application in investigating a sample comprising the steps of:
   a) providing a polarized beam of electromagnetic radiation and causing it to pass through a first aperture and thereafter become focused onto a sample with a first focusing means, such that said beam interacts with said sample to the end that energy is tangibly and concretely shifted between polarization orthogonal components thereof;
   b) intercepting said beam of electromagnetic radiation after it interacts with said sample with a second focusing means and therewith directing it to image said first aperture in the plane of a second aperture, which second aperture presents with a non-unity aspect ratio, such that at least some of said beam passes through said second aperture and enters an optical fiber;
   c) causing said optical fiber to carry the electromagnetic radiation entered thereinto to a detector such that said detector outputs at least one signal; and
   d) analyzing said at least one signal from said detector to arrive at sample characterizing data.

11. A method as in claim 10 which further comprises storing or displaying said at least one signal from said detector or said sample characterizing data.

12. A method as in claim 10 which is performed using a system for investigating samples with electromagnetic radiation having an equivalent to a spatial filter integrated therewithin, comprising:
   a) a source of electromagnetic radiation;
   b) a first aperture;
   c) a stage for supporting a sample;
   d) a focusing means;
   e) a second aperture, said second aperture having a hole therethrough with an aspect ratio other than unity;
   f) an optical fiber; and
   d) a detector;

such that in use said source of electromagnetic radiation provides a beam of electromagnetic radiation, at least some of which passes through said first aperture and proceeds to interact with a sample placed on said stage for supporting a sample, said beam, after interaction with said sample being caused to be focused by said focusing means and pass through said second aperture, then enter said optical fiber, which directs it into said detector;

said integrated equivalent to a spatial filter comprising said first aperture, said focusing means, said second aperture and said optical fiber, said elements being relatively positioned with respect to one another such that said focusing means images electromagnetic radiation passing through said first aperture, at the location of said second aperture, and such that at least some of said imaged electromagnetic radiation passing through said second aperture enters said optical fiber.

13. A system for investigating samples with electromagnetic radiation having an equivalent to a spatial filter integrated therewithin, comprising:
   a) a source of electromagnetic radiation;
   b) a first aperture;
   c) a first focusing means;
   d) a stage for supporting a sample;
   e) a second focusing means;
   f) a second aperture, said second aperture having a hole therethrough with an aspect ratio other than unity;
   g) an optical fiber; and
   h) a detector;

such that in use said source of electromagnetic radiation provides a beam of electromagnetic radiation, at least some of which passes through said first aperture and is focused by said first focusing means onto a sample placed on said stage for supporting a sample, said beam, after interaction with said sample being caused to be focused by said second focusing means and pass through said second aperture, then enter said optical fiber, which directs it into said detector;

said integrated equivalent to a spatial filter comprising said first aperture, said second focusing means, said second aperture and said optical fiber, said elements being relatively positioned with respect to one another such that said focusing means images electromagnetic radiation passing through said first aperture, at the location of said second aperture, and such that at least some of said imaged electromagnetic radiation passing through said second aperture enters said optical fiber.

14. A system as in claim 13 which further comprises a polarizer between said source of electromagnetic radiation and said stage for supporting a sample, and an analyzer between said stage for supporting a sample and said detector and in which said system is an ellipsometer or polarimeter.

15. A system as in claim 14, which further comprises at least one rotatable or rotating compensator located at, at least one location selected from the group consisting of:
   between said source of electromagnetic radiation and said stage for supporting a sample; and
   between said stage for supporting a sample and said detector.

16. A system as in claim 13 which further comprises a second spatial filter present between said source of electromagnetic radiation and said detector, said second spatial filter comprising a sequence of:
   a focusing means;
   an aperture having a hole therethrough with an aspect ratio selected from the group consisting of:
   unity; and
   other than unity; and
   a collimating means;

such that in use said source of electromagnetic radiation provides a beam of electromagnetic radiation, at least some of which is directed to interact with a sample placed on said stage for supporting a sample, said beam, after interaction with said sample being caused to enter said detector, at least some of said electromagnetic radiation that reaches said detector also pass passing through said spatial filter.

17. A system as in claim 13, wherein said hole in said second aperture having an aspect ratio other than unity is characterized by each dimension thereof being a selection from the group consisting of:
   said dimension is smaller than the diameter of said optical fiber;
   said dimension is the same diameter of said optical fiber; and
   said dimension is larger than the diameter of said optical fiber.

18. A system as in claim 13 which further comprises a collimating means after said stage for supporting a sample and before said second focusing means.

19. A method of providing a small spot size beam of electromagnetic radiation for application in investigating a sample comprising the steps of:
   a) providing a system for investigating samples with electromagnetic radiation having an equivalent to a spatial filter integrated therewithin, comprising:
      1) a source of electromagnetic radiation;
      2) a first aperture;
      3) a first focusing means;
      4) a stage for supporting a sample;
      5) a second focusing means;
      6) a second aperture, said second aperture having a hole therethrough with an aspect ratio other than unity;
      7) an optical fiber; and
      8) a detector;

such that in use said source of electromagnetic radiation provides a beam of electromagnetic radiation, at least some of which passes through said first aperture and is focused by said first focusing means onto a sample placed on said stage for supporting a sample, such that said beam interacts with said sample to the end that energy is tangibly and concretely shifted between polarization orthogonal components thereof, and after interaction with said sample being caused to be focused by said second focusing means and pass through said second aperture, then enter said optical fiber, which directs it into said detector;

said integrated equivalent to a spatial filter comprising said first aperture, said second focusing means, said second aperture and said optical fiber, said elements being relatively positioned with respect to one another such that said focusing means images electromagnetic radiation passing through said first aperture, at the location of said second aperture, and such that at least some of said imaged electromagnetic radiation passing through said second aperture enters said optical fiber;

b) causing said source of electromagnetic radiation to provide a beam of electromagnetic radiation and direct it to pass through said first aperture, first focusing means and interact with a sample on said stage for supporting a sample, them pass through said second focusing means, pass through said second aperture having a hole therethrough with an aspect ratio other than unity, enter said optical fiber and therevia enter said detector; such that said detector outputs at least one signal; and c) analyzing said at least one signal from said detector to arrive at sample characterizing data.

20. A method as in claim 19, in which at least one of said system first focusing means and said second focusing means is caused to comprise a functional combination of collimating and focusing means.

\* \* \* \* \*